US009016942B2

(12) United States Patent
Guo et al.

(10) Patent No.: US 9,016,942 B2
(45) Date of Patent: Apr. 28, 2015

(54) FOLDABLE PRESSING DEVICE AND X-RAY MACHINE

(75) Inventors: Can Guo, Shanghai (CN); Guo Jun Han, Shanghai (CN); Wen Ting Rui, Shanghai (CN); Yun Ping Wang, Shanghai (CN); Ning Tao Yang, Suzhou (CN)

(73) Assignee: Siemens Aktiengesellschaft, München (DE)

( * ) Notice: Subject to any disclaimer, the term of this patent is extended or adjusted under 35 U.S.C. 154(b) by 441 days.

(21) Appl. No.: 13/451,366

(22) Filed: Apr. 19, 2012

(65) Prior Publication Data

US 2012/0269328 A1 Oct. 25, 2012

(30) Foreign Application Priority Data

Apr. 20, 2011 (CN) .......................... 2011 1 0099823

(51) Int. Cl.
*A61B 6/04* (2006.01)
*A61B 6/00* (2006.01)

(52) U.S. Cl.
CPC .............. *A61B 6/0414* (2013.01); *A61B 6/0421* (2013.01); *A61B 6/4458* (2013.01); *A61B 6/4476* (2013.01); *A61B 6/4482* (2013.01)

(58) Field of Classification Search
CPC ....... A61B 6/04; A61B 6/0414; A61B 6/0421
USPC .................................. 378/204, 208
See application file for complete search history.

(56) References Cited

U.S. PATENT DOCUMENTS

| 6,726,642 B2 | 4/2004 | Danielsson et al. |
| 8,011,828 B2 * | 9/2011 | Beimler et al. ............... 378/189 |
| 8,113,711 B2 * | 2/2012 | Beimler et al. ............... 378/189 |
| 2008/0294264 A1 | 11/2008 | Beimler et al. |

FOREIGN PATENT DOCUMENTS

DE   600 15 183 T2   2/2006

OTHER PUBLICATIONS

German Office Action dated Mar. 15, 2013 for corresponding German Patent Application No. DE 10 2012 204 814.6 with English translation.

* cited by examiner

*Primary Examiner* — Allen C. Ho
(74) *Attorney, Agent, or Firm* — Lempia Summerfield Katz LLC

(57) ABSTRACT

Disclosed in the present embodiments are a foldable pressing device and an X-ray machine. The foldable pressing device includes a motor, a lifting member, a pressing member, a linear guide member with a stop position, a pulling member and a resilient member. The lifting member, driven by the motor, causes a sliding element in the linear guide member with a stop position and the pressing member to move upwards. When the sliding element arrives at an uprising stop position, the pressing member, under the effect of the lifting member and the pulling member, overcomes the resistance of the resilient member to realize the folding thereof. The lifting member, driven by the motor, drives the pressing member to move downwards, and the pressing member is unfolded under the effect of the resilient member.

20 Claims, 5 Drawing Sheets

FOLDABLE PRESSING DEVICE AND X-RAY MACHINE

This application claims the benefit of CN 201110099823.0, filed on Apr. 20, 2011.

TECHNICAL FIELD

The present embodiments relate to the field of X-ray machines.

BACKGROUND

X-ray machines are widely applied in various fields such as health care, science education, industry, etc. The X-ray machine applied in the health care field is used to carry out imaging by irradiating X-rays onto a film after the X-rays penetrate the human body according to the fact that the densities of tissue structures such as muscle and bone are different.

When carrying out imaging on a patient, in order to obtain a clearer focus of the image and better image effect, a pressing device may be used. In order to make it convenient for the patient to get on or off the patient bed, the pressing device may be designed as one of two types of structure: a turnable pressing device or a foldable pressing device.

The turnable pressing device utilizes a guide control combining a helical groove with a linear groove, so that when the patient is getting on or off the patient bed, the pressing device turns to one side by way of the helical groove. When inspection is carried out, the pressing device enters into the linear groove by way of the helical groove so as to press on the organ of the patient.

A foldable pressing device may be assembled from several segments of structures. When the pressing device is lifted to a certain height, the pressing device starts to turn and fold in the same plane, making it easy for the patient to get on or off the patient bed. When the folded pressing device is descended to a certain position, the pressing device turns and unfolds again in the same plane, and is held in the unfolded state during the continuous descending motion, so as to carry out pressing on the patient.

The foldable pressing device is being used more, since the spatial utilization rate is high, the foldable pressing device is graceful in motion, and the potential risk is relatively small. The foldable pressing device is to realize multiple motions, and each motion has corresponding position requirements. The currently available foldable pressing devices may be controlled by more than two motors, resulting in that, for the foldable pressing devices in the prior art, both the structure and the motion control thereof are complicated. The price for the foldable pressing devices in the prior art is high, and the pressing device in the prior art may be used merely in some high-end products.

U.S. patent application US20080294264A1 discloses a shoulder type hinge, in which said shoulder type hinge includes a mechanical arm, and the mechanical arm is composed of an upper arm and a lower arm, the motions of the upper arm and the lower arm being coupled by two effectively connected rolling wheels.

SUMMARY AND DESCRIPTION

The present embodiments may obviate one or more of the drawbacks or limitations in the related art. For example, a foldable pressing device having relatively simple structure and motion control is provided.

The foldable pressing device may include a single motor, a lifting member, a pressing member, a linear guide member with a stop position, a pulling member and a resilient member. The lifting member includes a lift driving element driven by the motor and a lift motion element for mating with the lift driving element. The lift motion element includes a connecting end pivotally connected to the pressing member in the vertical direction. The pressing member includes a pressing head, a first pressing rod and a second pressing rod. The pressing head is fixedly connected to a first end of the first pressing rod. A second end of the first pressing rod is connected to a first end of the second pressing rod by a rotary wheel that rotates synchronously with the first pressing rod. A second end of the second pressing rod is connected to the connecting end of the lift motion element by a non-rotary wheel. The second pressing rod is rotatable about the non-rotary wheel within a defined angle range under a working position, and a linear guide structure is provided on the second pressing rod in the length direction. The linear guide member with stop position includes a linear guide element used vertically with the position thereof being fixed. The linear guide member also includes a first sliding element slidable relative to the linear guide element, and a second sliding element connected to the first sliding element by a rotating shaft. The second sliding element is slidable relative to the linear guide structure on the second pressing rod. The upper end of the linear guide element has a first stop block for restricting the position of the first sliding element. The pulling member includes a first pulling element. A first end of the first pulling element is fixed onto the rotary wheel after having been wound counter-clockwise around the rotary wheel for at least a first defined length. A second end of the first pulling element is fixed onto the non-rotary wheel after having been wound clockwise around the non-rotary wheel for at least a second defined length. The resilient member includes a first resilient element and a second resilient element. One end of the first resilient element is fixed onto the second pressing rod, and the other end of the first resilient element is fixed onto the lift motion element, thus causing the second pressing rod to be held in the working position relative to the lift motion element under the effect of the resilient force of the first resilient element. One end of the second resilient element is fixed onto the first pressing rod, and the other end of the second resilient element is fixed onto the second pressing rod, thus causing the first pressing rod to be held in the same linear relationship with the second pressing rod under the effect of the resilient force of the second resilient element.

In one embodiment, a wheel disk is provided outside the second sliding element. The pulling member further includes a second pulling element, with a first end of the second pulling element being fixed onto the rotary wheel after having been wound clockwise around the rotary wheel for at least a third defined length. A second end of the second pulling element is fixed onto the wheel disk after having been wound clockwise around the wheel disk of the second sliding element for at least a fourth defined length.

According to one embodiment, the second end of the second pressing rod has, on an end face facing the lift motion element, a plane of a first defined dimension and a cylindrical face of a second defined dimension, with the plane being located above the cylindrical face. Alternatively or additionally, a working position stop protrusion is provided on the second sliding element, and a second stop block is provided on the first sliding element for restricting the position of the working position stop protrusion.

The linear guide structure on the second pressing rod is a hollow sliding slot, and the second sliding element is a sliding slot guide block running through the sliding slot. Alternatively, the linear guide structure on the second pressing rod is a groove provided on one side or both sides, and the second sliding element is a groove guide block mating with the groove.

The lift driving element is a screw rod, and the lift motion element is a screw nut. In one embodiment, the lift driving element is a belt wheel, and the lift motion element is a belt. In another embodiment, the lift driving element is a sprocket, and the lift motion element is a chain.

According to one embodiment, the first resilient element is a coil spring, a spring or a leaf spring, and the second resilient element is a coil spring, a spring or a leaf spring.

According to another embodiment, the first pulling element is a steel cable, a chain or another flexible member or part with an elastic modulus and strength meeting the requirements thereof.

According to one embodiment, the second pulling element is a steel cable, a chain or another flexible member or part with an elastic modulus and strength meeting the requirements thereof.

The first pressing rod has a fitting slot for folding at a position close to the second end thereof and for mating with the first end of the second pressing rod in a folded state.

The foldable pressing device further includes an enclosure located at the periphery of the main body part of the foldable pressing device.

The X-ray machine of the present embodiments is an X-ray machine including the abovementioned foldable pressing device.

In the present embodiments, the pressing rod is divided into two parts. The folding and unfolding of the pressing device is achieved using the combination effect of the pulling member and the resilient member by way of using a motor to drive the lifting member and the linear guide member with a stop position. Both the structure and the motion control of the pressing device are relatively simple, the price thereof is low, and the mounting and maintenance thereof are convenient.

DETAILED DESCRIPTION OF THE PRESENT EMBODIMENTS

In order to make the object, technical solutions and advantages of the present embodiments more apparent, the present embodiments are further described in detail hereinafter by way of example.

Figure 1:
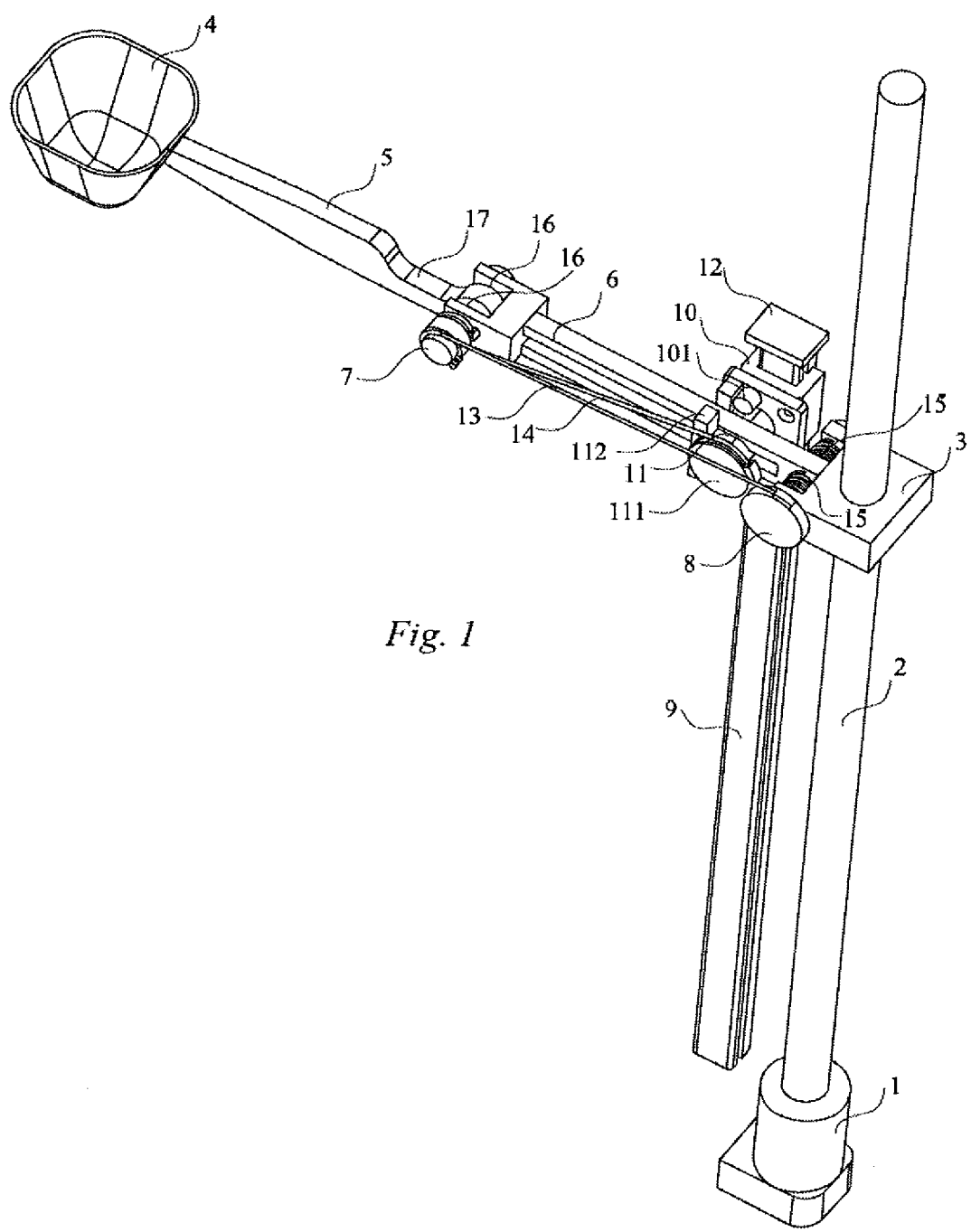
FIG. 1 is a structural view of one embodiment of a foldable pressing device in an unfolded state.
Figure 2:
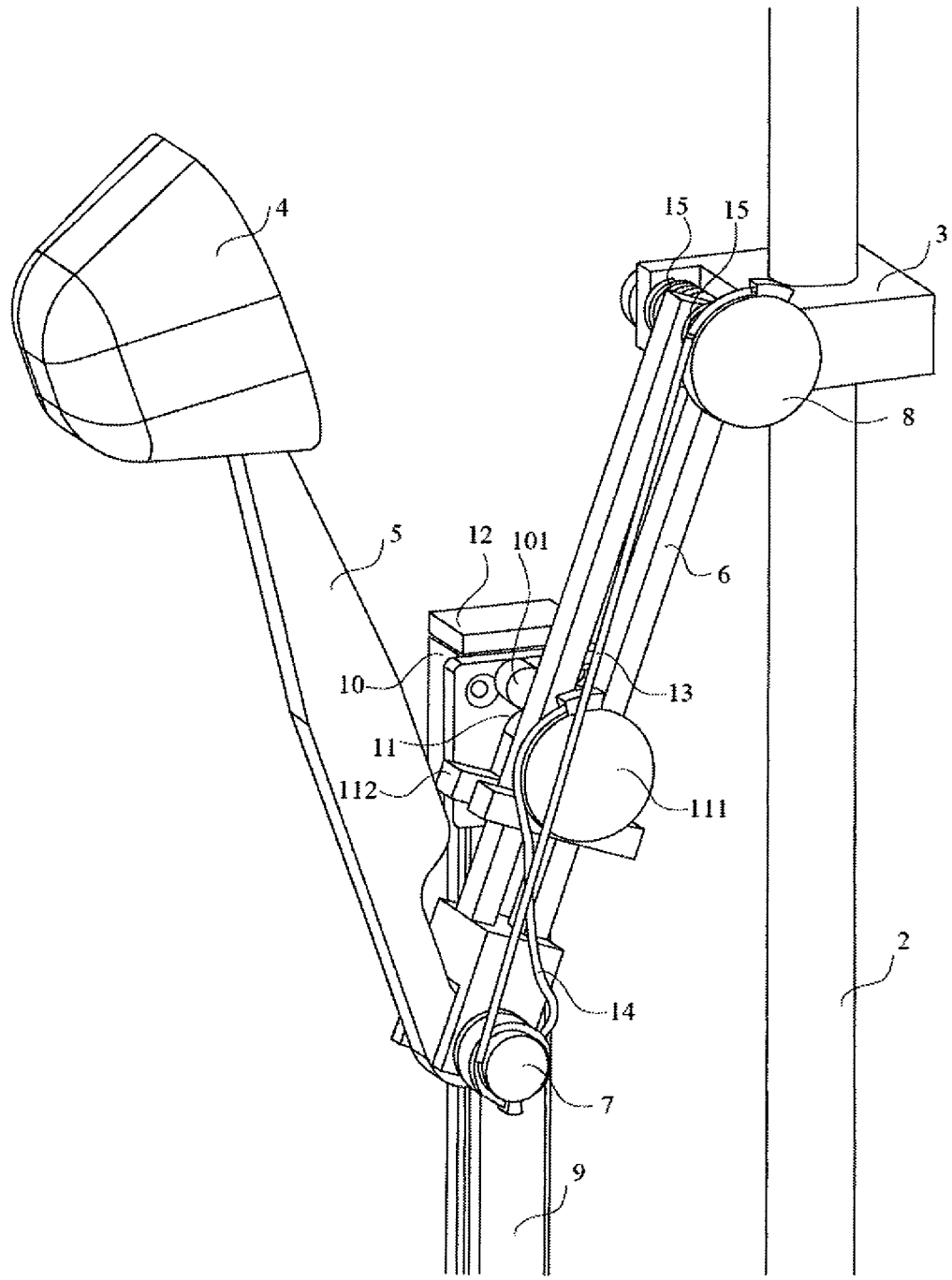
FIG. 2 is a structural view of one embodiment of the foldable pressing device in a folded state.

FIG. 1 is a structural view of one embodiment of a foldable pressing device in an unfolded state. FIG. 2 is a structural view of one embodiment of the foldable pressing device in a folded state. In the present description, the embodiments of the foldable pressing device are described in detail mainly according to the orientation shown in FIG. 1; unless specifically noted, the upper, lower, left, right, front, back, vertical and horizontal orientations involved in the description for the sake of explanation are all in terms of the visual angle shown in FIG. 1.

In conjunction with FIGS. 1 and 2, the foldable pressing device includes a single motor 1 (e.g., a motor), a lifting member, a pressing member, a linear guide member with a stop position, a pulling member and a resilient member.

The lifting member includes a lift driving element 2 driven by the motor 1 and a lift motion element 3 for mating with the lift driving element 2. The lift motion element 3 includes a connecting end pivotally connected to the pressing member in a vertical direction, as shown on the left side of the lift motion element 3. In the foldable pressing device shown in FIG. 1, the lift driving element 2 and the lift motion element 3 are a screw rod and a screw nut, respectively. The lift driving element 2 and the lift motion element 3 may also be a belt wheel and a belt, respectively, a sprocket and a chain, respectively, or another member or part operable to realize the lift function.

The pressing member includes a pressing head 4, a first pressing rod 5 and a second pressing rod 6. The pressing head 4 is fixedly connected to a first end of the first pressing rod 5. A second end of the first pressing rod 5 is connected to a first end of the second pressing rod 6 by a rotary wheel 7 that rotates synchronously with the first pressing rod 5. A second end of the second pressing rod 6 is connected to the connecting end of the lift motion element 3 (e.g., the screw nut 3 as shown in FIG. 1) by a non-rotary wheel 8. The second pressing rod 6 is rotatable around the non-rotary wheel 8 within a defined angle range under a working position, and the second pressing rod 6 is provided with a linear guide structure in the length direction thereof. The linear guide structure may be a hollow sliding slot, as shown in FIG. 1, and may also be a groove provided on one side or both sides.

The linear guide member with a stop position includes a linear guide element 9 used vertically with a position of the linear guide element 9 being fixed. The linear guide member with the stop position also includes a first sliding element 10 slidable relative to the linear guide element 9, and a second sliding element 11 connected to the first sliding element 10 by a rotating shaft (not shown in FIG. 1 or 2). The second sliding element 11 is slidable relative to the linear guide structure on the second pressing rod 6, and during the relative sliding, the second sliding element 11 rotates around an axial center of a rotating shaft between the second sliding element 11 and the first sliding element 10 along with the rotation of the second pressing rod 6. An upper end of the linear guide element 9 has a first stop block 12 for restricting the position of the first sliding element 10. In one embodiment, the linear guide element 9 may be a guide rail, as shown in FIG. 1. The linear guide element 9 may also be another element having a linear guide structure, and accordingly, the first sliding element 10 is an element mating therewith (e.g., a sliding block). In one embodiment, the second sliding element 11 has a structure mating with the linear guide structure on the second pressing rod 6. For example, corresponding to the hollow sliding slot of the second pressing rod 6, as shown in FIG. 1, the second sliding element 11 is a sliding slot guide block running through the sliding slot. In another embodiment, corresponding to the groove provided on one side or both sides of the second pressing rod 6, the second sliding element 11 may be a groove guide block mating with the groove. In addition, a wheel disk 111 is provided outside the second sliding element 11.

The pulling member includes a first pulling element 13 and a second pulling element 14. A first end of the first pulling element 13 is fixed onto the rotary wheel 7 after having been wound counter-clockwise around the rotary wheel 7 for a first defined length. A second end of the first pulling element 13 is fixed onto the non-rotary wheel 8 after having been wound clockwise around the non-rotary wheel 8 for a second defined length. In one embodiment, the fixed first pulling element 13 is always in a tense state. A first end of the second pulling element 14 is fixed onto the rotary wheel 7 after having been wound clockwise around the rotary wheel 7 for a third defined length. A second end of the second pulling element 14 is fixed onto the wheel disk 111 after having been wound clockwise around the wheel disk 111 of the second sliding element 11 for a fourth defined length. The fixed second pulling element 14 is in a tense state when the pressing device is in an unfolded state. The particular values of the first defined length, the second defined length, the third defined length, and the fourth defined length may be defined according to practical requirements, such that when the non-rotary wheel 8 drives the second end of the first pulling element 13 into an upward motion, the first end of the first pulling element 13 is operable to drive the rotary wheel 7 to rotate clockwise. When the pressing device is in the unfolded state and is pressing on a patient, the second pulling element 14 may endure the upward torque applied by the pressing force to the first pressing rod 5, thus avoiding the clockwise rotation of the rotary wheel 7 under the effect of the torque. In order to achieve that when the non-rotary wheel 8 drives the second end of the first pulling element 13 into an upward motion, the first end of the first pulling element 13 is operable to drive the rotary wheel 7 to rotate clockwise, the rotating radius of the rotary wheel 7 may be smaller than that of the non-rotary wheel 8.

In one embodiment, there may be two of the first pulling element 13 and two of the second pulling element 14 in addition to the first pulling element 13 and the second pulling element 14 provided on the left side of the second pressing rod 6, as shown in FIG. 1. One of the first pulling elements 13 and one of the second pulling elements 14 may also be provided on another side of the second pressing rod 6. Accordingly, the second sliding element 11 may also be provided with a wheel disk 111 on the corresponding side. The first pulling element 13 may be a steel cable, a chain, or another flexible member or part with an elastic modulus and strength meeting the requirements thereto. The second pulling element may also be a steel cable, a chain, or another flexible member or part with an elastic modulus and strength meeting the requirements thereof. In one embodiment, the elastic modulus is 0 or a value as small as possible.

The resilient member includes a first resilient element 15 and a second resilient element 16 (not shown in FIG. 2). One end of the first resilient element 15 is fixed onto the second pressing rod 6, and the other end of the first resilient element 15 is fixed onto the lift motion element 3, thus causing the second pressing rod 6 to be held in the working position relative to the lift motion element 3 under the effect of the resilient force of the first resilient element 15. One end of the second resilient element 16 is fixed onto the first pressing rod 5, and the other end of the second resilient element 16 is fixed onto the second pressing rod 6, thus causing the first pressing rod 5 to be kept in the same linear relationship with the second pressing rod 6 under the effect of the resilient force of the second resilient element 16. The first resilient element 15 may be a coil spring, a spring a leaf spring, or another type of resilient element. The second resilient element 16 may also be a coil spring, a spring, a leaf spring, or another type of resilient element.

When the foldable pressing device is to be folded, driven by the motor 1, the lift driving element 2 drives the lift motion element 3 into an upward motion. At this moment, under the effect of the linear guide member and the resilient member, the lift motion element 3 drives the first pressing rod 5 and the second pressing rod 6 into an upward motion. At the same time, the second sliding element 11 and the first sliding element 10 move upwards along with the first pressing rod 5 and the second pressing rod 6. When the first sliding element 10 contacts the first stop block 12 located at the upper end of the linear guide element 9, the first sliding element 10 and the second sliding element 11 stop upward motions. At this moment, the lift motion element 3 continues to rise. The second pressing rod 6, under the effect of the linear guide member thereof and the second sliding element 11, overcomes the resilient force of the first resilient element 15 and makes a counter-clockwise rotating motion relative to the lift motion element 3 and the non-rotary wheel 8. At this moment, because both ends of the first pulling element 13 are fixed, the length thereof is always kept constant. Thus, during the motion of the second pressing rod 6 relative to the non-rotary wheel 8, the first pulling element 13 overcomes the resilient force of the second resilient element 16, and drives the rotary wheel 7, which rotates synchronously along with the first pressing rod 5, into rotation. This causes the first pressing rod 5 to rotate clockwise relative to the second pressing rod 6, thereby realizing folding. At the same time, the second pulling element 14, which is kept in the tense state when the pressing device is in the unfolded state, because both ends thereof are fixed and the length thereof may be kept constant, is loosened during the folding process of the pressing device due to the shortening of the relative length between two fixed ends thereof.

In one embodiment, the first pressing rod 5 is provided with a fitting slot 17 for folding at a position close to the second end thereof and for mating with the first end of the second pressing rod 6 in the folded state.

When a patient is to be inspected, the pressing device begins to descend. In other words, driven by the motor 1, the lift driving element 2 drives the lift motion element 3 into a downward motion. At this moment, the first pressing rod 5 and the second pressing rod 6 gradually loosen under the effect of the resilient member and arrive in straightness, because there is a limit for the rotation angle of the second pressing rod 6 relative to the lift motion element 3. When the pressing device is straight, the second pressing rod 6 may no longer rotate upward relative to the lift motion element 3. At this moment, the lift motion element 3 drives the first sliding element 10, the second sliding element 11 and the pressing rods (e.g., including the first pressing rod 5 and the second pressing rod 6) into a downward motion together. The pressing device is kept in a straight state, while at the same time, the second pulling element 14 recovers to a tense state. When the pressing device starts to press on the patient due to the effect of the second pulling element 14, the first pressing rod 5 does not rotate relative to the second pressing rod 6 because of the load and torque borne by the first pressing rod 5. The pressing device is thereby operable to normally press the organ of the patient and carry out a series of inspections. In one embodiment, if the resilient force of the resilient member is adequate for bearing the load and torque generated while pressing on the patient, the second pulling element 14 may be omitted, and accordingly, the wheel disk 111 may not be provided outside the second sliding element 11.

During practical implementation, in order to realize synchronous rotation along with the first pressing rod 5 during the folding, a non-circular structure connection may be used between the rotary wheel 7 and the first pressing rod 5 (e.g., hemicycle, over-hemicycle, or polygon structure connections such as triangle or quadrangle). Interference fit connections or other connections may also be adopted. A circular structure connection is provided between the rotary wheel 7 and the second pressing rod 6, so that the first pressing rod 5 and the rotary wheel 7 are rotatable relative to the second pressing rod 6. A non-circular structure connection is provided between the non-rotary wheel 8 and the lift motion element 3, so as to realize non-rotation. A circular structure connection is provided between the non-rotary wheel 8 and the second pressing rod 6, so that the second pressing rod 6 is rotatable about the non-rotary wheel 8.

In order to avoid the second pressing rod 6 from rotating to a position above the working position around the non-rotary wheel 8 in the working state and thus losing the pressing force, the second pressing rod 6 is rotatable around the non-rotary wheel 8 within a defined angle range under the working position during the folding. A stop position structure may be provided on the second end of the pressing rod 6, so as to prevent the second pressing rod 6 from rotating around the non-rotatory wheel 8 to a position above the working position.

Figure 3:
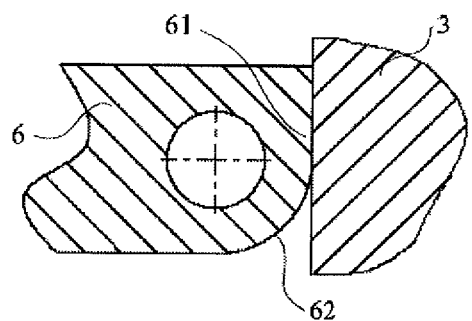
FIG. 3 is a partial sectional view of connecting ends of one embodiment of a second pressing rod and a lift motion element.

In one embodiment, a stop position structure may be provided on an end face of the second pressing rod 6 facing the lift motion element 3. The specific structure is as shown in FIG. 3, which is a partial sectional view of the connecting ends of the second pressing rod 6 and the lift motion element 3. FIG. 3 shows that a plane 61 of a first defined dimension and a cylindrical face 62 of a second defined dimension are provided on the end face of the second end of the second pressing rod 6 facing the lift motion element 3. The plane 61 is located above the cylindrical face 62.

Alternatively, a working position stop protrusion 112 may also be provided on the second sliding element 11. A second stop block 101 for restricting the position of the working position stop protrusion 112 is provided on the first sliding element 10. The working position stop protrusion 112 on the second sliding element 11 may also prevent the second pressing rod 6 from swinging from left to right.

During practical application, the abovementioned two stop position manners may be adopted simultaneously. Any one of the two stop position manners may be adopted, or other forms of stop position manners may also be adopted.

Figure 4:
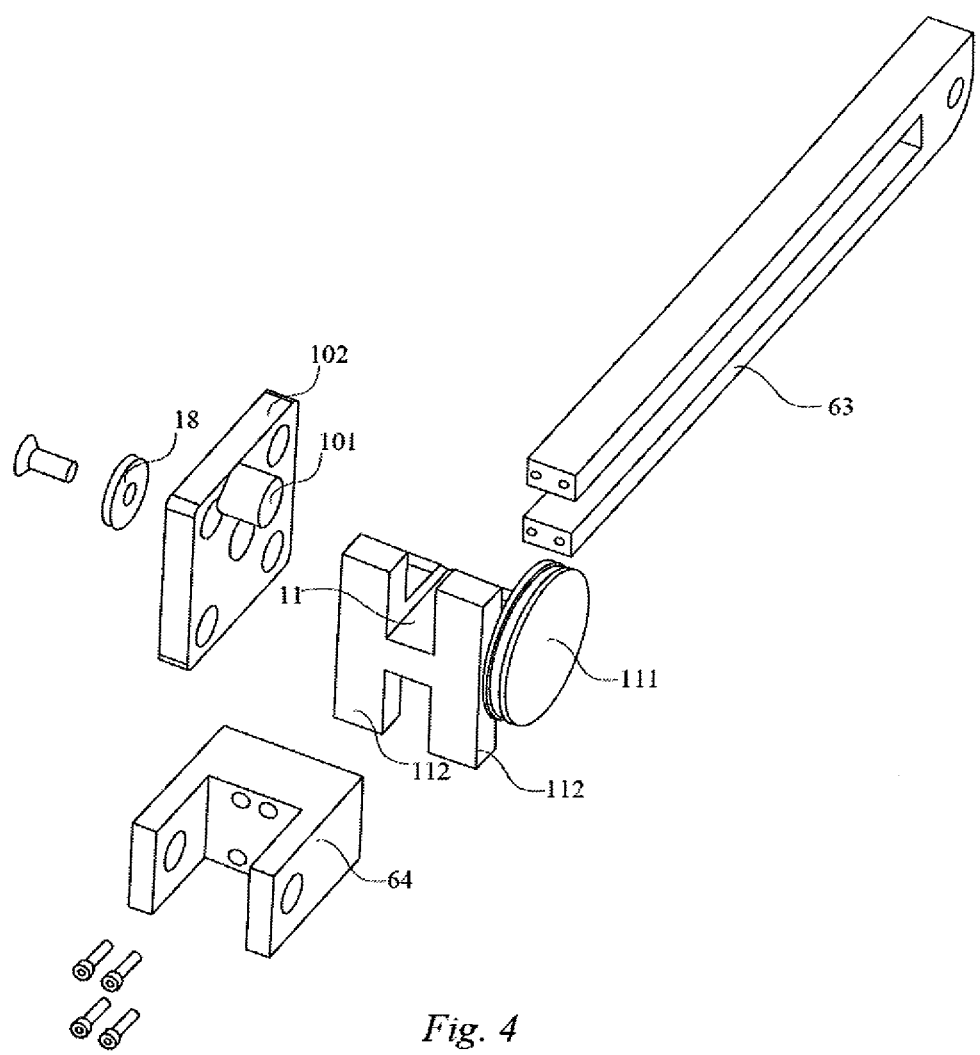
FIGS. 4 and 5 are schematic views illustrating, from different angles, the exemplary assembly relationship between the second pressing rod and a second sliding element shown in FIG. 1, and the exemplary assembly relationship between the second sliding element and a first sliding element, respectively.
Figure 5:
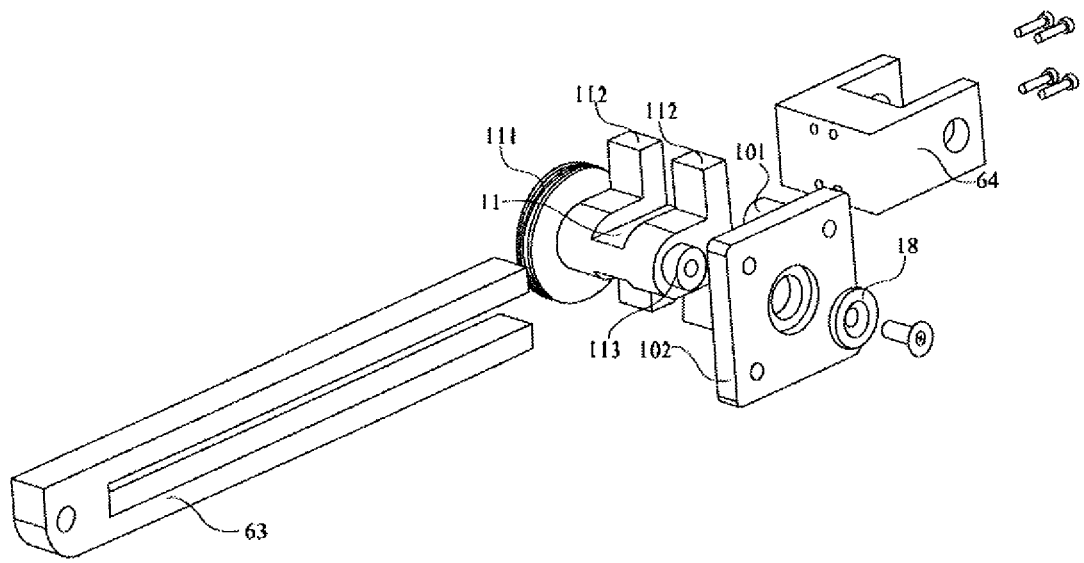

FIGS. 4 and 5 illustrate, from different angles, schematic views of the assembly relationship between the second pressing rod 6 with the hollow sliding slot in FIG. 1 and the second sliding element 11 and the assembly relationship between the second sliding element 11 and the first sliding element 10, respectively. As shown in FIGS. 4 and 5, the second pressing rod 6 includes two parts: a U-shape pressing rod body 63 with a hollow sliding slot, and a connecting end 64 for pivotally connecting to the first pressing rod 5. The U-shape closed end of the pressing rod body 63 is used to connect to the lift motion element 3 by the non-rotary wheel 8. The U-shape closed end is provided with a rotating hole for mating with the non-rotary wheel 8. The U-shape open end of the pressing rod body 63 is provided with a screw hole that may be used to connect to the connecting end 64 by connecting pieces such as a screw or a bolt. During assembly, the second sliding element 11 may be assembled into the hollow slot from the U-shape open end of the pressing rod body 63; subsequently, the U-shape open end of the pressing rod body 63 is connected to the connecting end 64.

For the sake of easy assembling, the first sliding element 10 may include a connecting plate 102. The second sliding element 11 may be connected to the sliding body of the first sliding element 10 by the connecting plate 102, as shown in FIGS. 4 and 5. The second sliding element 11 has, on the side close to the first sliding element 10, a rotating shaft 113 that rotates synchronously with the second sliding element 11. The rotating shaft 113 may be inserted into the through-via of the connecting plate 102 so as to connect to a washer 18 on the other side of the connecting plate 102 by a connecting piece such as a screw or a bolt, thereby assembling the second sliding element 11 onto the connecting plate 102. The second sliding element 11 is rotatable relative to the connecting plate 102. The connecting plate 102 is fixed onto the sliding body of the first sliding element 10 by a connecting piece such as a screw or a bolt. In order to be easy to assemble with the sliding body of the first sliding element 10, the connecting plate 102 is provided, on the side away from the second sliding element 11, with a sink hole that is coaxial with the through-via. The diameter of the sink hole is larger than the through-via for accommodating the washer 18 in the sink hole.

The second stop block 101 for restricting the position of the working position stop protrusion 112 on the second sliding element 11 may be provided on the connecting plate 102.

Figure 6:
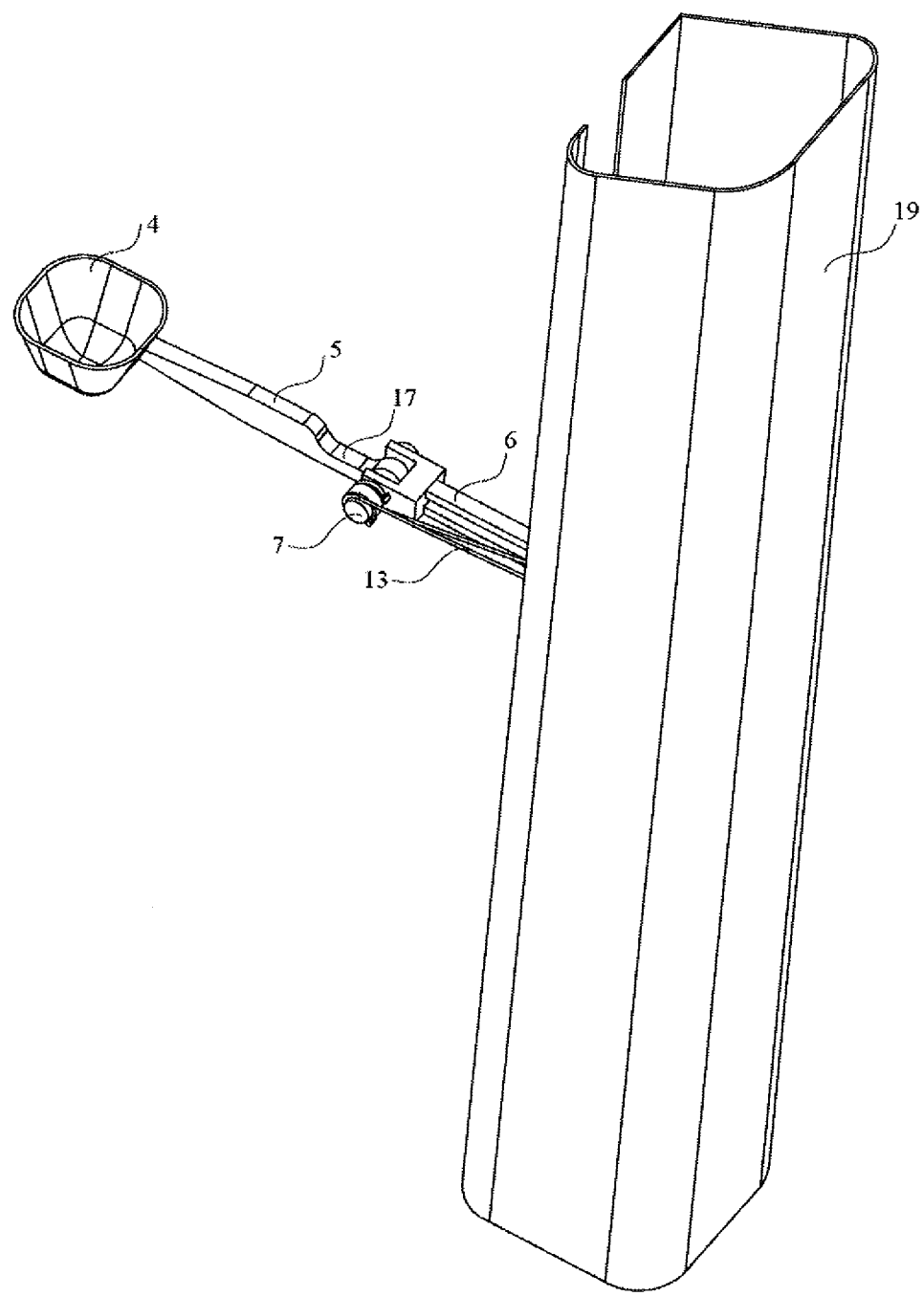
FIG. 6 is a structural view of one embodiment of the foldable pressing device having an enclosure in the folded state according.

In one embodiment, the foldable pressing device may include, as shown in FIG. 6, an external enclosure 19 that is located at the periphery of the main body part of the foldable pressing device.

The X-ray machine of the present embodiments includes the above-described foldable pressing device.

A foldable pressing device and an X-ray machine are disclosed in the present embodiments. The foldable pressing device includes a single motor, a lifting member, a pressing member, a linear guide member with a stop position, a pulling member and a resilient member. The lifting member, driven by the motor, drives the sliding element in the linear guide member with a stop position and the pressing member to move upwards. When the sliding element arrives at an uprising stop position, the pressing member, under the effect of the lifting member and the pulling member, overcomes the resistance of the resilient member to realize the folding thereof. The lifting member, driven by the motor, drives the pressing member to move downwards, and the pressing member is unfolded under the effect of the resilient member. The folding of the pressing device is realized by a single motor. During the folding, the lifting member, driven by the motor, drives the sliding element in the linear guide member with a stop position and the pressing member to move upwards. When the sliding element arrives at an uprising stop position, the pressing member, under the effect of the lifting member and the pulling member, overcomes the resistance of the resilient member to realize the folding thereof. During the unfolding, the lifting member, driven by the motor, drives the pressing member to move downwards, and the pressing member is unfolded under the effect of the resilient member. Both the structure and motion control of the foldable pressing device are relatively simple, the price thereof is low, and the mounting and maintenance thereof are convenient.

What are described above are embodiments of the present invention and are not intended to limit the present invention. Any modifications, equivalents, and/or improvements within the spirit and principle of the present invention should be covered by the scope of protection of the present invention.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A foldable pressing device comprising:
   a motor;
   a lifting member;
   a pressing member; and
   a linear guide member comprising a stop position, a pulling member, and a resilient member,
   wherein the lifting member comprises a lift driving element driven by the motor and a lift motion element for mating with the lift driving element, the lift motion element having a connecting end pivotally connected to the pressing member in a vertical direction,
   wherein the pressing member comprises a pressing head, a first pressing rod, a second pressing rod, a linear guide structure, a rotary wheel, and a non-rotary wheel, the pressing head being fixedly connected to a first end of the first pressing rod, a second end of the first pressing rod being connected to a first end of the second pressing rod by the rotary wheel, which rotates synchronously with the first pressing rod, a second end of the second pressing rod being connected to the connecting end of the lift motion element by the non-rotary wheel, the second pressing rod being rotatable around the non-rotary wheel within a defined angle range under a working position, the linear guide structure being provided on the second pressing rod in a length direction of the second pressing rod,
   wherein the linear guide member with the stop position comprises a linear guide element used vertically with a position of the linear guide element being fixed, the linear guide member further comprising a first sliding element being slidable relative to the linear guide element, the linear guide member further comprising a second sliding element and a rotating shaft, the second sliding element being connected to the first sliding element by the rotating shaft, the second sliding element being slidable relative to the linear guide structure on the second pressing rod, an upper end of the linear guide element having a first stop block for restricting a position of the first sliding element,
   wherein the pulling member comprises a first pulling element, a first end of the first pulling element being fixed onto the rotary wheel after having been wound counterclockwise around the rotary wheel for at least a first defined length, and a second end of the first pulling element being fixed onto the non-rotary wheel after having been wound clockwise around the non-rotary wheel for at least a second defined length, and
   wherein the resilient member comprises a first resilient element and a second resilient element, one end of the first resilient element being fixed onto the second pressing rod, the other end of the first resilient element being fixed onto the lift motion element, thus causing the second pressing rod to be held in the working position relative to the lift motion element under the effect of a resilient force of the first resilient element, one end of the second resilient element being fixed onto the first pressing rod, the other end of the second resilient element being fixed onto the second pressing rod, thus causing the first pressing rod to be held in the same linear relationship with the second pressing rod under the effect of a resilient force of the second resilient element.

2. The foldable pressing device as claimed in claim 1, further comprising a wheel disk outside the second sliding element,
   wherein the pulling member further comprises a second pulling element, a first end of the second pulling element being fixed onto the rotary wheel after having been wound clockwise around the rotary wheel for at least a third defined length, a second end of the second pulling element being fixed onto the wheel disk after having been wound clockwise around the wheel disk of the second sliding element for at least a fourth defined length.

3. The foldable pressing device as claimed in claim 2, wherein the second pulling element is a steel cable, a chain or another flexible member or part.

4. The foldable pressing device as claimed in claim 1, wherein the second end of the second pressing rod has, on an end face facing the lift motion element, a plane of a first defined dimension and a cylindrical face of a second defined dimension, the plane being located above the cylindrical face, and
   wherein the linear guide member further comprises a working position stop protrusion provided on the second sliding element, and a second stop block for restricting a position of the working position stop protrusion provided on the first sliding element.

5. The foldable pressing device as claimed in claim 1, wherein the linear guide structure on the second pressing rod is a hollow sliding slot, and the second sliding element is a sliding slot guide block running through the hollow sliding slot, or
   wherein the linear guide structure on the second pressing rod is a groove provided on one side or both sides of the second pressing rod, and the second sliding element is a groove guide block mating with the groove.

6. The foldable pressing device as claimed in claim 1, wherein the lift driving element is a screw rod, and the lift motion element is a screw nut,
   wherein the lift driving element is a belt wheel, and the lift motion element is a belt, or
   wherein the lift driving element is a sprocket, and the lift motion element is a chain.

7. The foldable pressing device as claimed in claim 1, wherein the first resilient element is a coil spring, a spring or a leaf spring, and
   wherein the second resilient element is a coil spring, a spring or a leaf spring.

8. The foldable pressing device as claimed in claim 1, wherein the first pulling element is a steel cable, a chain or another flexible member or part.

9. The foldable pressing device as claimed in claim 1, wherein the first pressing rod has a fitting slot for folding at a position close to the second end of the first pressing rod, the fitting slot being for mating with the first end of the second pressing rod when in a folded state.

10. The foldable pressing device as claimed in claim 1, further comprising an enclosure located at a periphery of a portion of the foldable pressing device.

11. An X-ray machine comprising:
    a foldable pressing device comprising:
    a motor;
    a lifting member;
    a pressing member; and
    a linear guide member comprising a stop position, a pulling member, and a resilient member,
    wherein the lifting member comprises a lift driving element driven by the motor and a lift motion element for mating with the lift driving element, the lift motion element having a connecting end pivotally connected to the pressing member in a vertical direction, wherein the pressing member comprises a pressing head, a first pressing rod, a second pressing rod, a linear guide structure, a rotary wheel, and a non-rotary wheel, the pressing head being fixedly connected to a first end of the first pressing rod, a second end of the first pressing rod being connected to a first end of the second pressing rod by the rotary wheel, which rotates synchronously with the first pressing rod, a second end of the second pressing rod being connected to the connecting end of the lift motion element by the non-rotary wheel, the second pressing rod being rotatable around the non-rotary wheel within a defined angle range under a working position, the linear guide structure being provided on the second pressing rod in a length direction of the second pressing rod, wherein the linear guide member with the stop position comprises a linear guide element used vertically with a position of the linear guide element being fixed, the linear guide member further comprising a first sliding element being slidable relative to the linear guide element, the linear guide member further comprising a second sliding element and a rotating shaft, the second sliding element being connected to the first sliding element by the rotating shaft, the second sliding element being slidable relative to the linear guide structure on the second pressing rod, an upper end of the linear guide element having a first stop block for restricting a position of the first sliding element, wherein the pulling member comprises a first pulling element, a first end of the first pulling element being fixed onto the rotary wheel after having been wound counterclockwise around the rotary wheel for at least a first defined length, and a second end of the first pulling element being fixed onto the non-rotary wheel after having been wound clockwise around the non-rotary wheel for at least a second defined length, and wherein the resilient member comprises a first resilient element and a second resilient element, one end of the first resilient element being fixed onto the second pressing rod, the other end of the first resilient element being fixed onto the lift motion element, thus causing the second pressing rod to be held in the working position relative to the lift motion element under the effect of a resilient force of the first resilient element, one end of the second resilient element being fixed onto the first pressing rod, the other end of the second resilient element being fixed onto the second pressing rod, thus causing the first pressing rod to be held in the same linear relationship with the second pressing rod under the effect of a resilient force of the second resilient element.

12. The X-ray machine as claimed in claim 11, wherein the foldable pressing device further comprises a wheel disk outside the second sliding element, and wherein the pulling member further comprises a second pulling element, a first end of the second pulling element being fixed onto the rotary wheel after having been wound clockwise around the rotary wheel for at least a third defined length, a second end of the second pulling element being fixed onto the wheel disk after having been wound clockwise around the wheel disk of the second sliding element for at least a fourth defined length.

13. The X-ray machine as claimed in claim 12, wherein the second pulling element is a steel cable, a chain or another flexible member or part.

14. The X-ray machine as claimed in claim 11, wherein the second end of the second pressing rod has, on an end face facing the lift motion element, a plane of a first defined dimension and a cylindrical face of a second defined dimension, the plane being located above the cylindrical face, and wherein the linear guide member further comprises a working position stop protrusion provided on the second sliding element, and a second stop block for restricting a position of the working position stop protrusion provided on the first sliding element.

15. The X-ray machine as claimed in claim 11, wherein the linear guide structure on the second pressing rod is a hollow sliding slot, and the second sliding element is a sliding slot guide block running through the hollow sliding slot, or wherein the linear guide structure on the second pressing rod is a groove provided on one side or both sides of the second pressing rod, and the second sliding element is a groove guide block mating with the groove.

16. The X-ray machine as claimed in claim 11, wherein the lift driving element is a screw rod, and the lift motion element is a screw nut, wherein the lift driving element is a belt wheel, and the lift motion element is a belt, or wherein the lift driving element is a sprocket, and the lift motion element is a chain.

17. The X-ray machine as claimed in claim 11, wherein the first resilient element is a coil spring, a spring or a leaf spring, and wherein the second resilient element is a coil spring, a spring or a leaf spring.

18. The X-ray machine as claimed in claim 11, wherein the first pulling element is a steel cable, a chain or another flexible member or part.

19. The X-ray machine as claimed in claim 11, wherein the first pressing rod has a fitting slot for folding at a position close to the second end of the first pressing rod, the fitting slot being for mating with the first end of the second pressing rod when in a folded state.

20. The X-ray machine as claimed in claim 11, further comprising an enclosure located at a periphery of a portion of the foldable pressing device.

* * * * *